(12) United States Patent
Carley et al.

(10) Patent No.: US 8,076,315 B2
(45) Date of Patent: Dec. 13, 2011

(54) PHARMACOLOGICAL TREATMENTS FOR SLEEP DISORDERS (APNOE) WITH PROSTANOID RECEPTOR ANTAGONISTS

(75) Inventors: David W. Carley, Evanston, IL (US); Miodrag Radulovacki, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 571 days.

(21) Appl. No.: 12/090,131

(22) PCT Filed: Oct. 13, 2006

(86) PCT No.: PCT/US2006/039895
§ 371 (c)(1),
(2), (4) Date: May 12, 2008

(87) PCT Pub. No.: WO2007/047372
PCT Pub. Date: Apr. 26, 2007

(65) Prior Publication Data
US 2008/0261922 A1 Oct. 23, 2008

Related U.S. Application Data

(60) Provisional application No. 60/726,901, filed on Oct. 14, 2005.

(51) Int. Cl.
*A61K 31/66* (2006.01)
*A61P 25/00* (2006.01)
*A01N 43/00* (2006.01)

(52) U.S. Cl. .................... 514/75; 514/211.01
(58) Field of Classification Search .................. 514/75, 514/211.01
See application file for complete search history.

(56) References Cited

U.S. PATENT DOCUMENTS

2004/0105819 A1* 6/2004 Hale et al. .................. 424/45
2006/0094082 A1* 5/2006 Varadhachary et al. ..... 435/69.1

FOREIGN PATENT DOCUMENTS
EP 0 300 676 7/1988

OTHER PUBLICATIONS

Krieger et al., "Urinary excretiobn of prostanoids during sleep in obstructive sleep apnoea patients", Clinical and Experimental Pharmacology and Physiology 1991 18:551-555.
Clement et al., "The effects of PGF2alpha on respiratory and cardiovascular variables in PIG", Prostaglandins and Medicine 1979 3:367-376.
Lee et al., "Pulmonary chemoreflex sensitivity is enhanced by prostaglandin E2 in anesthetized rats", J. Appl. Physiol. 1995 79(5):1679-1686.
Karlsson et al., "Respiratory and cardiovascular effects of inhaled and intravenous bradykinin, PGE2, and PGF2alpha in dogs", J. Appl. Physiol. 1993 74(5):2380-2386.
Guerra et al., "Prostaglandin E2 causes hypoventilation and apnea in newborn lambs", J. Appl. Physiol. 1988 64 (5):2160-2166.
Lim et al., "Aminophylline for the prevention of apnea during prostaglandin E1 infusion", Pediatrics 2003 112(1):e27-e29.
Taguchi et al., "Prostaglandin E2 inhalation increases the sensation of dyspnea during exercise", Am Rev Respir Dis 1992 145:1346-1349.
Mohammed et al., "Effects of aerosol-applied capsaicin, histamine and prostaglandin E2 on airway sensory receptors of anaesthetized cats", Journal of Physiology 1993 469:51-66.
Scott et al., "Chemical mediators of the muscle ergoreflex in chronic heart failure", Circulation 2006 106:214-220.
Clement et al., "Role of hypotension induced by PGI2 on the control of depth and frequency of breathing", Prostaglandins and Medicine 1980 5:415-423.
Clement et al., Effects of PGF2alpha on the EMG of costal and crural parts of the diaphragm of the newborn pig, Prostglandins Leukotrienes and Essential Fatty Acids 1991 43:167-173.
Clement et al., "PGF2alpha and breathing pattern in newborn pigs", Prostglandins Leukotrienes and Essential Fatty Acids 1990 40:103-107.
Preas et al., "Effect of endotoxin on ventilation and breath variability", Am J Respir Crit Care Med 2001 164:620-626.
Fontana et al., "Prostaglandin synthesis blockade by ketoprofen attenuates respiratory and cardiovascular responses to static handgrip", J. Appl. Physiol. 1994 78(2):449-457.
Carrithers et al., :Thromboxane A2 mimetic U-46619 induces systemic and pulmonary hypertension and delayed tachypnea in the goat, J. Appl. Physiol. 1994 77(3):1466-1473.
Midorikawa et al., "Effects of prostaglandin E2 inhalation on hypercapnic response in normal subjects", Am J Respir Crit Care Med 1994 150:1592-1597.

* cited by examiner

*Primary Examiner* — Barbara P Badio
*Assistant Examiner* — Sara E Townsley
(74) *Attorney, Agent, or Firm* — Licata & Tyrell, P.C.

(57) ABSTRACT

This invention is directed to methods for preventing or ameliorating sleep-related breathing disorders. The method comprises administration to a patient in need thereof an effective dose of one or a combination of prostanoid receptor antagonists (eg. ramatroban, ifetroban, diphloretin, phosphate, polyphloretin phosphate, seratrodast, SC19220). The prostanoid receptor antagonist or combination of prostanoid receptor antagonists can be administered in conjunction with one or more serotonin receptor agonists, one or more cannabinoids receptor agonists, one or more serotonin reuptake inhibitors, one or more noradrenalin reuptake inhibitors, a combination of reuptake inhibitors, an inhibitor of prostanoid synthesis, or any combination of the foregoing.

1 Claim, 1 Drawing Sheet

FIG. 1

PHARMACOLOGICAL TREATMENTS FOR SLEEP DISORDERS (APNOE) WITH PROSTANOID RECEPTOR ANTAGONISTS

INTRODUCTION

This application is the National Phase of PCT/US2006/039895 filed Oct. 13, 2006, which claims the benefit of priority from U.S. Provisional Patent Application No. 60/726,901, filed Oct. 14, 2005.

BACKGROUND OF THE INVENTION

1. Field of the Invention

The invention generally relates to methods for pharmacological treatment of breathing disorders and, more specifically, to administration of agents or compositions having prostanoid receptor antagonist activity for the alleviation of sleep apnea (central and obstructive) and other sleep-related breathing disorders.

2. Background of the Related Art

Over the past several years much effort has been devoted to the study of a discrete group of breathing disorders that occur primarily during sleep with consequences that may persist throughout the waking hours in the form of daytime sleepiness, and result in substantial economic loss (e.g., thousands of lost man-hours) or cause employment safety issues (e.g., employee non-attentiveness during operation of heavy-machinery). Sleep-related breathing disorders are characterized by repetitive reduction in breathing (hypopnea), periodic cessation of breathing (apnea), or a continuous or sustained reduction in ventilation.

In general, sleep apnea is defined as an intermittent cessation of airflow at the nose and mouth during sleep. By convention, apneas of at least 10 seconds in duration have been considered important; however, in most individuals, apneas are 20-30 seconds in duration and may be as long as 2-3 minutes. While there is some uncertainty as to the minimum number of apneas that should be considered clinically important, by the time most individuals come to a doctor's attention they have at least 10 to 15 events per hour of sleep.

Sleep apneas have been classified into three types: central, obstructive (the most common type), and mixed. In central sleep apnea, the neural drive to all respiratory muscles is transiently abolished. In obstructive sleep apneas, airflow ceases despite continuing respiratory drive because of occlusion of the oropharyngeal airway. Mixed apneas, which consist of a central apnea followed by an obstructive component, are a variant of obstructive sleep apnea.

Obstructive sleep apnea syndrome (OSAS) has been identified in as many as 24% of working adult men and 9% of similar women, with peak prevalence in the sixth decade. Habitual heavy snoring, which is an almost invariant feature of OSAS, has been described in up to 24% of middle aged men, and 14% of similarly aged women, with even greater prevalence in older subjects. A definitive event of obstructive sleep apnea syndrome is the occlusion of the upper airway, frequently at the level of the oropharynx. The resultant apnea generally leads to a progressive-type asphyxia until the individual is briefly aroused from the sleeping state, thereby restoring airway patency and airflow.

The recurrent episodes of nocturnal asphyxia and of arousal from sleep that characterize OSAS lead to a series of secondary physiologic events, which in turn give rise to the clinical complications of the syndrome. The most common manifestations are neuropsychiatric and behavioral disturbances that are thought to arise from the fragmentation of sleep and loss of slow-wave sleep induced by the recurrent arousal responses. Nocturnal cerebral hypoxia also may play an important role. The most pervasive manifestation is excessive daytime sleepiness. OSAS is now recognized as a leading cause of daytime sleepiness and has been implicated as an important risk factor for such problems as motor vehicle accidents. Other related symptoms include, but are not limited to, intellectual impairment, memory loss, personality disturbances, and impotence.

The other major manifestations are cardiorespiratory in nature and are thought to arise from the recurrent episodes of nocturnal asphyxia. Most individuals demonstrate a cyclical slowing of the heart during the apneas to 30 to 50 beats per minute, followed by tachycardia of 90 to 120 beats per minute during the ventilatory phase. A small number of individuals develop severe bradycardia with asystoles of 8 to 12 seconds in duration or dangerous tachyarrhythmias, including unsustained ventricular tachycardia. OSAS also aggravates left ventricular failure in patients with underlying heart disease. This complication is most likely due to the combined effects of increased left ventricular afterload during each obstructive event, secondary to increased negative intrathoracic pressure, recurrent nocturnal hypoxemia, and chronically elevated sympathoadrenal activity.

Central sleep apnea is less prevalent as a syndrome than OSAS, but can be identified in a wide spectrum of patients with medical, neurological, and/or neuromuscular disorders associated with diurnal alveolar hypoventilation or periodic breathing. A definitive event in central sleep apnea is transient abolition of central drive to the ventilatory muscles. The resulting apnea leads to a primary sequence of events similar to those of OSAS. Several underlying mechanisms can result in cessation of respiratory drive during sleep. First are defects in the metabolic respiratory control system and respiratory neuromuscular apparatus. Other central sleep apnea disorders arise from transient instabilities in an otherwise intact respiratory control system. In individuals with clinically significant central sleep apnea, the primary sequence of events that characterize the disorder leads to prominent physiological and clinical consequences. In those individuals with central sleep apnea alveolar hypoventilation syndrome, daytime hypercapnia and hypoxemia are usually evident and the clinical picture is dominated by a history of recurrent respiratory failure, polycythemia, pulmonary hypertension, and right-sided heart failure. Complaints of sleeping poorly, morning headache, and daytime fatigue and sleepiness are also prominent. In contrast, in individuals whose central sleep apnea results from an instability in respiratory drive, the clinical picture is dominated by features related to sleep disturbance, including recurrent nocturnal awakenings, morning fatigue, and daytime sleepiness.

Currently, the most common and most effective treatment for adults with sleep apnea and other sleep-related breathing disorders are mechanical forms of therapy that deliver positive airway pressure (PAP). Under PAP treatment, an individual wears a tight-fitting plastic mask over the nose when sleeping. The mask is attached to a compressor, which forces air into the nose creating a positive pressure within the patient's airways. The principle of the method is that pressurizing the airways provides a mechanical "splinting" action that prevents airway collapse and therefore, obstructive sleep apnea. Although an effective therapeutic response is observed in most patients who undergo PAP treatment, many patients cannot tolerate the apparatus or pressure and refuse treatment. Moreover, covert monitoring studies clearly demonstrate that long-term compliance with PAP treatment is very poor.

A variety of upper airway and craniofacial surgical procedures have been attempted for treatment of OSAS. While adenotonsillectomy appears to be an effective cure for OSAS in many children, upper airway surgery is rarely curative in adult OSAS patients. Surgical "success" is generally taken to be a 50% reduction in apnea incidence and there are no useful screening methods to identify the individuals that would benefit from the surgery versus those who would not derive a benefit.

Pharmacological treatments of several types have been attempted in patients with sleep apnea but, thus far, none have proven to be generally useful. (A recent systematic review of these attempts is provided by Smith & Quinnell, 2004, *Drugs* 64: 1385-1399.) A number of compounds have been tested because of their expected respiratory stimulant properties. These include: (1) acetazolamide, a carbonic anhydrase inhibitor that produced variable improvement in individuals with primarily central apneas, but caused an increase in obstructive apneas, (2) medroxyprogesterone, a progestin that has demonstrated no consistent benefit in OSAS, and (3) theophylline, a compound usually used for the treatment of asthma that may benefit patients with central apnea, but appears to be of no use in adult patients with obstructive apnea.

Other attempted pharmacological treatments include administration of adenosine, adenosine analogs and adenosine reuptake inhibitors (see e.g., U.S. Pat. No. 5,075,290). Specifically, adenosine, a ubiquitous compound within the body that is elevated in individuals with OSAS, has been shown to stimulate respiration and is somewhat effective in reducing apnea in an animal model of sleep apnea.

Other possible pharmacological treatment options for OSAS include agents that stimulate brain activity or are opioid antagonists. Specifically, since increased cerebral spinal fluid opioid activity has been identified in OSAS, central stimulants or opioid antagonists were thought to be a helpful treatment of OSAS. As it turns out, doxapram, a compound that stimulates the central nervous system and carotid body chemoreceptors, was found to decrease the length of apneas, but did not alter the average arterial oxygen saturation in individuals with obstructive sleep apnea. The opioid antagonist naloxone, which is known to stimulate ventilation, was only slightly helpful in individuals with obstructive sleep apnea.

Several agents that act on neurotransmitters and neurotransmitter systems involved in respiration have been tested in individuals with OSAS. Most of these compounds have been developed as anti-depressant medications that work by increasing the activity of monoamine neurotransmitters, including norepinephrine, dopamine, and serotonin. For example, protriptyline, a tricyclic antidepressant, has been tested in several small trials with variable results and frequent and significant side effects. As serotonin may promote sleep and stimulate respiration, tryptophan, a serotonin precursor, as well as selective serotonin reuptake inhibitors (SSRIs) have been tested in individuals with OSAS. Although a patent has been issued for the use of the serotonin reuptake inhibitor, fluoxetine (U.S. Pat. No. 5,356,934) for treating sleep apnea, initial evidence suggests that these compounds may yield measurable benefits in only approximately 50% of individuals with OSAS. The rationale for using SSRIs such as fluoxetine or paroxetine to treat sleep apnea syndrome rests in part on their ability to stimulate upper airway motor outputs. Applications of serotonin to the floor of the fourth ventricle (Rose et al., 1995, *Respir. Physiol.* 101: 59-69) or into the hypoglossal motor nucleus (Kubin et al., 1992, *Neurosci. Lett.* 139: 243-248) produced upper airway motor activation in cats; effects that appear to be mediated predominantly by serotonin subtype 2 receptors (Okabe et al., 1997, *Respir. Physiol.* 110: 151-160; Volgin et al., 2003, *Eur. J. Neurosci.* 17: 1179-1188). Conversely, systemic administration of 5-hydroxytryptamine2 receptor antagonists to English bulldogs reduced electrical activation of upper airway muscles, diminishing upper airway cross-sectional area (Veasey et al., 1996, *Am. J. Respir. Crit. Care Med.* 153: 776-786). These observations provide a likely explanation for the improvements in sleep-disordered breathing observed in some patients following SSRI treatment, but illustrate that to be generally effective, SSRI treatment must be combined with another agent.

Buspirone, a specific serotonin subtype 1 receptor agonist that stimulates respiration (Mendelson et al., 1990, *Am. Rev. Respir. Dis.* 141: 1527-1530), has been shown to reduce apnea index in 4 of 5 patients with sleep apnea syndrome (Mendelson et al., 1991, *J. Clin. Psychopharmacol.* 11: 71-72) and to eliminate post-surgical apneustic breathing in one child (Wilken et al., 1997, *J. Pediatr.* 130: 89-94). Despite this limited experience in the art, the use of serotonin agonists to treat apneas has been disclosed in several issued patents (U.S. Pat. Nos. 6,552,062; 6,433,175; 6,432,956; 6,387,907; 6,356,598; 6,380,238; and 6,303,608).

Somewhat paradoxically in view of the foregoing, serotonin antagonists also have been examined as drug treatments for sleep apnea in humans and in animal models of sleep related breathing disorders. In rats that express frequent central apneas during all sleep stages, the serotonin antagonists ondansetron, R-zacopride, and mirtazapine all have been shown to reduce apnea frequency. Mirtazapine was able to reduce apnea frequency by 50% in one study of OSAS patients, whereas ondansetron failed to demonstrate any effect in another study. Nevertheless, several patents have been issued describing the use of serotonin antagonists to treat OSAS (U.S. Pat. Nos. 6,835,740; 6,727,242; 6,649,183; 6,613,779; 6,576,670; 6,559,165; 6,552,062; 6,548,082; 6,465,490; 6,331,536; 6,303,595; 6,277,864; 6,143,792; and 6,048,879).

Several other medical treatments for sleep apnea have been disclosed, including the administration of: the nucleoside uptake blocker dipyridamole (U.S. Pat. No. 5,502,067), pilocarpine compounds (U.S. Pat. No. 5,407,953) and ubidecarenone (U.S. Pat. No. 5,422,374), sodium proton pump inhibitors (U.S. Pat. No. 7,049,333)) and sodium protein pump inhibitors (U.S. Pat. No. 7,049,333). Stimulation of various structures, such as the pontine intertrigeminal region (Radulovacki et al., 2003, *Brain Research* 975: 66-72; Radulovacki et al., 2004, *Sleep* 27: 383-387) and the pedunculopontine tegmentum (Saponjic et al. 2003. *Resp. Physiol. Neurobiol.* 138: 223-237) by the excitatory amino acid glutamate has been shown to evoke immediate apnea, and a glutamate release inhibitor was shown to reduce the frequency of central apneas in a rat model (Radulovacki et al. 2001. *J. Pharm. Pharmacol.* 53: 1555-9). One patent has been issued for the use of glutamate antagonists or release inhibitors to treat OSAS (U.S. Pat. No. 6,555,564). In addition, the cannabinoid receptor agonist Δ9-tetrahydrocannabinol and the endogenous fatty acid amide oleamide were shown to reduce sleep apneas in an animal model (Carley et al., 2002, *Sleep* 25: 391-398; U.S. Patent Application Publication No. 20040127572 describes this approach).

Specific modulation of CRTH2, COX-2 and FAAH for the treatment of pain and inflammation as well as sleep-related breathing disorders is disclosed in U.S. patent application Ser. No. 11/028,896. Treatment of sleep disorders with a derivative of antihistamine doxepin alone, or in combination with a prostaglandin, is provided in U.S. patent application Ser. No. 11/114,535. Prostanoids have been disclosed for the treatment of respiratory disorders such as asthma (U.S. Pat. No. 5,625,083) and prostaglandin $D_2$ antagonists have been provided for the treatment of sleep disorders as well as sleep-wake cycle disorders (U.S. patent application Ser. No. 10/780,441). However, specific inhibition of a prostanoid receptor for preventing or ameliorating a sleep-related breathing disorder is not suggested by these prior art references.

Nonetheless, no pharmacological agent or therapeutic regimen using a pharmaceutical formulation yet attempted has resulted in an efficacious treatment for any type of sleep apnea. Therefore, in view of the fact that the only viable treatment for individuals suffering from sleep-related breathing disorders is a mechanical form of therapy for which patient compliance is low, and that hopes for pharmacological treatments have yet to come to fruition, there remains a need for simple pharmacologically-based treatments that would offer benefits to a broad base of individuals suffering from a range of sleep-related breathing disorders. There also remains a need for a viable treatment of sleep-related breathing disorders that would have a high rate of patient compliance.

SUMMARY OF THE INVENTION

The invention is directed generally to providing pharmacological treatments for prevention or amelioration of sleep-related breathing disorders such as sleep apnea syndrome.

The invention is specifically directed to methods for preventing or ameliorating sleep-related breathing disorders, said methods comprising the step of administering an effective dose of a prostanoid receptor antagonist to a patient in need of a therapy for preventing or ameliorating sleep-related breathing disorders. The present invention is also directed to methods comprising the step of administering to a patient in need thereof a combination of prostanoid receptor antagonists for preventing or ameliorating sleep-related breathing disorders. The combination of prostanoid receptor antagonists may be directed to a single prostanoid receptor subtype or to more than one prostanoid receptor subtype.

The invention is further directed to methods for preventing or ameliorating sleep-related breathing disorders comprising the step of administering to a patient in need thereof one or a combination of prostanoid receptor antagonists in conjunction with a one or more serotonin receptor agonists for preventing or ameliorating sleep-related breathing disorders. The combination of prostanoid receptor antagonists may be directed to a single prostanoid receptor subtype or to more than one prostanoid receptor subtype and the combination of serotonin receptor agonists may be directed to a single serotonin receptor subtype or to more than one serotonin receptor subtype.

The invention is further directed to methods for preventing or ameliorating sleep-related breathing disorders comprising the step of administering to a patient in need thereof one or a combination of prostanoid receptor antagonists in conjunction with a one or more cannabimimetic agents including cannabinoid receptor agonists, cannabinoid membrane transport inhibitors and endocannabinoid breakdown inhibitors for preventing or ameliorating sleep-related breathing disorders. The combination of prostanoid receptor antagonists may be directed to a single prostanoid receptor subtype or to more than one prostanoid receptor subtype and the combination of cannabimimetic agents may be directed to a single cannabinoid receptor subtype or to more than one cannabinoid receptor subtype.

The invention is also directed to methods for preventing or ameliorating sleep-related breathing disorders comprising the step of administering to a patient in need thereof one or a combination of prostanoid receptor antagonists in conjunction with a serotonin reuptake inhibitor for preventing or ameliorating sleep-related breathing disorders. The combination of prostanoid receptor antagonists may be directed to a single prostanoid receptor subtype or to more than one prostanoid receptor subtype.

The invention is also directed to methods for preventing or ameliorating sleep-related breathing disorders comprising the step of administering to a patient in need thereof one or a combination of prostanoid receptor antagonists in conjunction with a noradrenalin reuptake inhibitor for preventing or ameliorating sleep-related breathing disorders. The combination of prostanoid receptor antagonists may be directed to a single prostanoid receptor subtype or to more than one prostanoid receptor subtype.

The invention is also directed to methods for preventing or ameliorating sleep-related breathing disorders comprising the step of administering to a patient in need thereof one or a combination of prostanoid receptor antagonists in conjunction with a combination of serotonin or noradrenalin reuptake inhibitors for preventing or ameliorating sleep-related breathing disorders. The combination of prostanoid receptor antagonists may be directed to a single prostanoid receptor subtype or to more than one prostanoid receptor subtype and the combination of serotonin or noradrenalin reuptake inhibitors may directed to either serotonin reuptake or to noradrenalin reuptake, or to both serotonin and noradrenalin reuptake inhibitors.

The invention is also directed to methods for preventing or ameliorating sleep-related breathing disorders comprising the step of administering to a patient in need thereof one or a combination of prostanoid receptor antagonists in conjunction with inhibitors of prostanoid synthesis.

Specific preferred embodiments of the invention will become evident from the following more detailed description of certain preferred embodiments and the claims.

DETAILED DESCRIPTION OF THE INVENTION

The invention provides methods for preventing or suppressing sleep-related breathing disorders, and in particular central and obstructive sleep apneas, by administering one or a combination of prostanoid receptor antagonists, directed at one or a plurality of prostanoid receptor subtypes. The prostanoid receptor antagonists are administered according to the inventive methods either per se or in combination with other agents, including but not limited to serotonin receptor agonists, serotonin reuptake inhibitors, noradrenaline reuptake inhibitors, combined serotonin/noradrenalin reuptake inhibitors, caimabimimetic agents including cannabinoid receptor agonists, cannabinoid membrane transport inhibitors and endocannabinoid breakdown inhibitors, and inhibitors of prostanoid synthesis.

Effective treatments for preventing or suppressing sleep-related breathing disorders include systemic administration of a prostanoid receptor antagonist either alone or in combination. In a preferred embodiment, the prostanoid receptor antagonist has activity only in the peripheral nervous system and/or does not cross the blood-brain barrier. In a more preferred embodiment, the prostanoid receptor antagonist displays activity to one or more prostanoid receptor types (e.g., DP, EP1, EP2, EP3, EP4, FP, IP, TP, and the like).

Exemplary prostanoid receptor antagonists include, but are not limited to, AH-6809, ONO-8711 and ONO-8713, L-161, 982 (4), AH-23848 (4), ONO-AE3-208 (4), SC19220, ONO-8711, SC51089, L-798,106, prostanoid receptor antisense oligonucleotides, ONO-8713, ONO-AE829, ONO-AE2-227, SC51322, ZD-6416, ONO-3144, ONO-3708, ONO-NT-12, SC-236, SC-299, SC-51234A, SKF-104493, SKF-105561, SKF-105809, SKF-106978, SKF-86002, SQ-28852, CGP-47969A, CGS-11776, FR-122047, L-640035, L-651392, L-651896, L-655240, L-657925, L-657926, L-745296, L-745337, L-746483, L-761066, L-768277, PD-138387, WY-48090, S-5751, BWA868C, ramatroban, Ifetroban, SQ-29548, ICI-192605, S-1452, FCE-27262, ONO-8809, ONO-NT-126, CBS-1108, L-636499, diphloretin phosphate, polyphloretin phosphate, BM-613, BM-500, BM-519, BM-567, BM-573, ONO-3708, seratrodast, GW627368 and taprostene, YM-158, YM-26734, YM-57158, Z-335, ZD-9583, and other prostanoid receptor antagonists as well known in the art and as disclosed in the Derwent Drug File database.

Additional prostanoid receptor antagonists include, but are not limited to, 6-[N-(2-benzyloxy-5- bromobenzyl)-N-ethylamino]pyridazine-3-carboxylic acid, 6-[N-(5-bromo-2-(2-methylprop-2-en-1-yloxy) benzyl)-N-ethylamino]pyridazine-3-carboxylic acid (disclosed in Example 15 of International Patent Publication No. WO 97/00864), N-propanesulphonyl-6-[N-(5-bromo-2-(cyclopropylmethoxy) benzyl)-N-ethylamino]pyridazine-3-carboxamide (disclosed in Example 14 of International Patent Publication No. WO 97/00863), N-(3,5-dimethylisoxazol-4-ylsulphonyl)-6-[N-(5-chloro-2-(2-methylpropoxy)benzyl-N-ethylamino]pyridazine-3-carboxamide (disclosed as compound number 1 in Example 8 of International Patent Publication No. WO 97/00863), 6-[N-(5-bromo-2-(cyclopropylnethoxy) benzyl)-N-ethylamino]pyridazine-3-carboxylic acid (disclosed in Example 3 of International Patent Publication No. 97/00863), and the like.

Further prostanoid receptor antagonists include, but are not limited to, those described in European Patent No. 0480641; European Patent No. 0534667; International Patent Application No. WO 96/03380; International Patent Application No. WO 96/06822; European Patent Application No. 0733033; European Patent Application No. 0847391; European Patent Application No. 0835246; European Patent Application No. 0752421; U.S. Pat. No. 5,504,077; European Patent No. 694546; U.S. Pat. No. 5,441,950; U.S. Pat. No. 5,420,270; U.S. Pat. No. 5,354,747; U.S. Pat. No. 5,354,746; U.S. Pat. No. 5,324,722; U.S. Pat. No. 5,304,644; U.S. Pat. No. 5,281, 590; International Patent Application No. WO 93/13082; European Patent No. 539977; International Patent Application No. WO 93/07132; European Patent No. 512400; European Patent No. 512399; European Patent No. 218077; European Patent No. 193822; U.S. Pat. No. 4,132,847; European Patent No. 0878465; European Patent No. 0300676; U.S. Pat. No. 4,775,680; European Patent No. 0845451; European Patent No. 0160408; International Patent Application No. WO 98/27053; and the like. All of the aforementioned patents and patent applications are incorporated by reference to the extent that they are not contradictory.

Exemplary serotonin receptor agonists include, but are not limited to, 8-OH-DPAT, almotriptan, sumatriptan, L694247 (2-[5-[3-(4-methylsulphonylamino)benzyl-1,2,4-oxadiazol-5-yl]-33 1H-indol-3yl]ethanamine), tegaserod, buspirone, ainitidan, zaiospirone, ipsapirone, gepirone, zolmitriptan, elitriptan, naratriptan, frovatriptan, rizatriptan, 311C90, a-Me-5-HT, BW723C86 (1-[5(2-thienylmethoxy)-1H-3-indolyl[propan-2-amine hydrochloride), MCPP (m-chlorophenylpiperazine), MK-212, bufotenin, 1-(m-trifluoromethylphenyl)-piperazine, N,N-dimethyl-5-methoxytryptamine, quipazine, venlafaxine, bifeprunox, donitriptan, and other serotonin agonists.

Exemplary serotonin reuptake inhibitors include, but are not limited to, fluoxetine, norfluoxetine, R(+)-fluoxetine, S(−)-fluoxetine, paroxetine, zimelidine, pirandamine, fluvoxamine, citalopram escitalopram, ORG6582, p-bromo EXP561, LM5008, sertraline, and other serotonin reuptake inhibitors.

Exemplary noradrenalin reuptake inhibitors include, but are not limited to, desipramine, nortriptyline, reboxetine, nisoxetine, atomoxetine, LY139603 (tomoxetine), and other noradrenalin reuptake inhibitors.

Exemplary combined serotonin/noradrenalin reuptake inhibitors include, but are not limited to, venlafaxine, milnacipran, duloxetine, pregabalin, LY248686, strattera, and other combined serotonin/noradrenalin reuptake inhibitors.

Exemplary inhibitors of prostanoid synthesis include, but are not limited to, indomethacin, ketorolac, acetylsalicylic acid, ibuprofen, sulindac, tolmetin, piroxicam, naproxen, and other prostanoid synthesis inhibitors.

Exemplary cannabimimetic agents include, but are not limited to: cannabinoid receptor agonists including, but not limited to, arachidonyl-2'-chloroethylamide, arachidonylcyclopropylamide, and methanandamide L-759633, L-759656, JWH-133, HU-308, and palmitoylethanolamide 9-tetrahydrocannabinol, 8-tetrahydrocannabinol, HU-210, CP55940, WIN55,212-2, O-1057, 2-arachidonoyl glycerol, anandamide, dexanabinol, nabilone, levonantradol, and N-(2-hydroxyethyl)hexadecanoamide; endocannabinoids including but not limited to oleamide, linoleoylethanolamide, and oleoylethanolamide; endocannabinoid breakdown inhibitors including but not limited to phenylmethylsulphonyl fluoride, palmitylsulphonyl fluoride, stearylsulphonyl fluoride, methyl arachidonyl fluorophosphonate, 2-octyl-gamma-bromoacetoacetate, ibuprofen, ketoralac, and flurdiprofen and O-1887; endocannabinoid membrane transport inhibitors including, but not limited to, AM404, VDM11, and arvanil; and the like.

Prostanoids are a family of autocrine mediators that act through multiple G-protein coupled receptors. Of relevance here, prostanoid receptors are widely expressed in both the peripheral and central nervous systems. Important endogenous prostanoids include at least the prostaglandin D, E, F, and I families and the thromboxanes. As reviewed by Ashby (see e.g., Ashby, 1998, *Biochem. Pharmacol.*, 55(3): 239-246), prostanoid receptors include at least: DP, EP1, EP2, EP3 (6 isoforms), EP4, FP, IP, and TP (2 isoforms). Previous studies on the effects of prostanoids (e.g., prostaglandins and thromboxanes) on respiration in several animal species have demonstrated variable responses. For example, administration of prostanoids has been shown to cause an increase (see e.g., Carrithers et al., 1994, *J. Appl. Physio.*, 77(3): 1466-1473; Fontana et al., 1995, *J. Appl. Physiol.*, 78(2): 449-457; Preas et al., 2001, *Am. J. Respir. Crit. Care Med.*, 164(4): 620-626) or a decrease (Clement et al., 1990, *Prostaglandins Leukot. Essent. Fatty Acids*, 40(2): 103-107; Clement et al., 1991, *Prostaglandins Leukot. Essent. Fatty Acids*, 43(3): 167-173) in the respiratory rate; increased tidal volume and minute ventilation (Clement et al., 1980, *Prostaglandins Med.*, 5(6): 415-423; Scott et al., 2002, *Circulation*, 106(2):

214-220); stimulation of rapidly adapting pulmonary stretch receptors (Mohammed et al., 1993, *J. Physiol.,* 469: 51-66) and diaphragm muscle (Clement et al., 1991, *Prostaglandins Leukot. Essent. Fatty Acids,* 43(3): 167-173); bronchoconstriction and dyspnea (Taguchi et al., 1992, *Am. Rev. Respir. Dis.,* 145(6): 1346-1349; Mohammed et al., 1993, *J. Physiol.,* 469: 51-66); decreased respiratory pattern variability (Clement et al., 1990, *Prostaglandins Leukot. Essent. Fatty Acids,* 40(2): 103-107) and increased hypercapnic respiratory responsiveness (Midorikawa et al., 1994, *Am. J Respir. Crit. Care Med.,* 150(6 Pt. 1): 1592-1597). In part, these disparate findings reflect differing effects of specific prostanoid ligands, prostanoid receptors, target tissues, species and experimental preparations. In addition, intravenous administration of prostaglandin E1 is well known to produce reflex apnea (Lim et al., 2003, *Pediatrics,* 112(1 Pt. 1): e27-29). Similarly, prostaglandin E2 and thromboxane A2 have been implicated in reflex apnea (Guerra et al., 1988, *J. Appl. Physiol.,* 64(5): 2160-2166; Karlsson et al., 1993, *J. Appl. Physiol.,* 74(5): 2380-2386) and prostaglandin E2 exacerbates the reflex apnea evoked by intravenous capsacin (Lee & Morton, 1995, *J. Appl. Physiol.,* 79(5): 1679-1686).

The foregoing studies reveal that activity at prostanoid receptors can initiate reflexive apnea, and suggest that the vagus nerves are necessary for prostanoids to exert this effect (Clement et al., 1979, *Prostaglandins Med.,* 3(6): 367-376). Vagus sensory neurons, with their cell bodies in the nodose ganglia, carry information to the brain from many receptors distributed throughout the lungs and chestwall. The observation that prostaglandins can produce reflex apnea and can potentiate reflex apnea produced by other natural and pharmacological stimuli (Lee & Morton, 1995, *J. Appl. Physiol.,* 79(5): 1679-1686) may account for blockade of vagus nerve-dependent reflexive apnea by prostanoid receptor antagonism.

This consequence of activity at prostanoid receptors is surprising because vagus nerve reflex apnea and sleep apnea are actually quite different. Reflex apnea occurs because of an external stimulus (e.g., fluid or foreign body aspiration, irritant inhalation, or excessive lung inflation), both in awake and in sleeping individuals, whereas sleep apnea occurs spontaneously and specifically during sleep. An agent useful to block one of these forms of apnea is not necessarily able to affect the other form of apnea. Indeed, in some instances a treatment for one form of apnea actually worsens the other form of apnea. Therefore, the observation that serotonin antagonists are able to reduce expression of both reflexive and sleep-related apnea (see e.g., Yoshioka et al., 1992, *J. Pharmacol. Exp. Ther.,* 260: 917-924; Radulovacki et al., 1998, *Sleep* 21(2): 131-136; Carley & Radulovacki, 1999, *Am. J. Respir. Crit. Care Med.,* 160(6): 1824-1829; Carley et al., 2001, *Pharmacol. Biochem. Behav.,* 69(1-2): 283-289) does not render obvious the use of a prostanoid antagonist in the treatment of sleep-related breathing disorders.

To illustrate the differences in treating sleep-related breathing disorders and reflex apnea, anti-histamines can effectively reduce reflexive apnea (Downs et al., 1995, *Laryngoscope,* 105(8 Pt. 1): 857-861), but they worsen sleep apnea (Ponsonby et al., 1997, *J. Paediatr. Child Health,* 33(4): 317-323). As another example, application of positive airway pressure produces immediate reflex apnea (Coon, 1994, J. Appl. Physiol., 76(6): 2546-2551), but treats sleep apnea (Haniff et al., 2004, *Cochrane Database Syst. Rev.,* 4: CD003531). Also, application of 10% $CO_2$ to the airways has no effect on reflex apnea, but effectively reduces sleep apnea (Badr et al., 1994, *Am. J Respir. Crit. Care Med.,* 150: 561-564). Finally, although beta-adrenergic agonists reduce reflex apnea (Grogaard & Sundell, 1983, *Pediatr. Res.,* 17(3): 213-219), beta-adrenergic agents have no effect on sleep apnea (Planes et al., 1999, *Sleep,* 22(4): 507-513). In view of these contradictions (reflex versus sleep apnea), an indication that a particular compound was shown, or hypothesized, to reduce reflex apnea cannot be taken as an indication that the compound is a suitable treatment for sleep apnea. A person skilled in the art will recognize that blocking reflex apnea does not reliably predict the ability of an agent to block sleep apnea.

Furthermore, experiments examining drug effects on reflex apnea are conducted on anesthetized animals (see e.g., Jacobs & Comroe, 1971, Circ. Res., 29: 145-155; Yoshioka et al., 1992, *J. Pharmacol. Exp. Ther.,* 260: 917-924). Anesthetized animals are not an accurate model of sleep. Control of breathing under anesthesia is profoundly different from control of breathing during sleep. This is particularly true for apnea expression. For example, rats spontaneously express sleep-related apnea, but spontaneous apnea is effectively blocked by general anesthesia of almost any sort (Strohl & Thomas, 1997, *Respir. Physiol.,* 110(2-3): 269-275).

As contemplated herein, any agent or combination of agents that interferes with the activity of endogenous prostanoids can be used as an effective treatment for sleep-related breathing disorders. Without being limited to any particular mechanism, the presumptive mechanism for this effect is interference with the activation of vagus sensory neurons by endogenous prostanoids.

To test the effects of prostanoid antagonists on sleep apnea, experiments are conducted in freely moving animals in order to assess whether blockade of prostanoid receptors inhibits expression of spontaneous apneas during non-rapid eye movement (NREM) sleep and rapid eye movement (REM) sleep. Experiments are also conducted to test the effects of prostanoid agonists and prostanoid antagonists, singly and in combination, in freely moving animals in order to assess whether increased activity at prostanoid receptors promotes sleep apneas. The following Examples illustrate this testing of the effects prostanoid receptor antagonist administration, and in particular the ability of these antagonists to cause suppression of spontaneous apneas during NREM and especially during REM sleep. The following Examples also illustrate testing of the capacity of prostanoid agonists to induce spontaneous apnea expression, and the ability of prostanoid antagonists to block this effect. The following Examples further describe the pharmacological profiles best suited for single agents or combinations of agents to successfully prevent or ameliorate sleep-related breathing disorders, including:

(a) a single agent or combination of agents having antagonistic activity at one or more prostanoid receptor types (DP, EP1, EP2, EP3, EP4, FP, IP, TP); or (b) a single agent or combination of agents having antagonistic activity at one or more prostanoid receptor types (DP, EP1, EP2, EP3, EP4, FP, IP, TP) in conjunction with either selective serotonin re-uptake inhibitor (SSRI) or serotonin/ noradrenalin reuptake inhibitor (SNRI) activity or both; or (c) a single agent or combination of agents having antagonistic activity at one or more prostanoid receptor types (DP, EP1, EP2, EP3, EP4, FP, IP, TP) in conjunction with serotonin receptor agonist activity; or (d) a single agent or combination of agents having antagonistic activity at one or more prostanoid receptor types (DP, EP1, EP2, EP3, EP4, FP, IP, TP) in conjunction with either cannabinoid receptor subtype 1 or cannabinoid receptor subtype 2 activity or both; or (e) a single agent or combination of agents having antagonistic activity at one or more prostanoid receptor types (DP, EP1, EP2, EP3, EP4, FP, IP, TP) in conjunction with an endocannabinoid breakdown inhibitor (e.g. a fatty acid amide hydrolase inhibitor); or (f) a single agent or combination of agents having antagonistic activity at one or more prostanoid receptor types (DP, EP1, EP2, EP3, EP4, FP, IP, TP) in conjunction with a cannabinoid membrane transport inhibitor; or (g) a single agent or combination of agents having antagonistic activity at one or more prostanoid receptor types (DP, EP1, EP2, EP3, EP4, FP, IP, TP) in conjunction with an agent or combination of agents that inhibit the synthesis of prostanoids; or (h) any combination of (a)-(g) above.

In conjunction with Examples 2 and 3 and the foregoing observations, sleep related breathing disorders (sleep apnea syndrome, apnea of infancy, Cheyne-Stokes respiration, sleep-related hypoventilation syndromes) can be effectively prevented or suppressed via systemic administration of:

(a) an agent or combination of agents exhibiting antagonism at one or more prostanoid receptor subtypes; or (b) an agent or combination of agents exhibiting antagonism at EP1 receptors; or (c) an agent or combination of agents exhibiting antagonism at EP2 receptors; or (d) an agent or combination of agents exhibiting antagonism at EP3 receptors; or (e) an agent or combination of agents exhibiting antagonism at EP4 receptors; or (f) an agent or combination of agents exhibiting antagonism at FP receptors; or (g) an agent or combination of agents exhibiting antagonism at IP receptors; or (h) an agent or combination of agents exhibiting antagonism at TP receptors; or (i) an agent or combination of agents exhibiting antagonism at one or more prostanoid receptors in combination with an agonist for either 5-hydroxytryptamine-1 or 5-hydroxytryptamine-2 receptors, or both; or (j) an agent or combination of agents exhibiting antagonism at one or more prostanoid receptors in combination with a cannabimimetic agent; or (k) an agent or combination of agents having antagonistic activity at one or more prostanoid receptor types (DP, EP1, EP2, EP3, EP4, FP, IP, TP) in conjunction with an agent or combination of agents that inhibit the synthesis of prostanoids; or (l) agents that exhibit both the proper antagonistic and agonistic pharmacological profile (i.e., an agent that is both an agonist/mimetic and antagonist at the receptor subtypes set forth above).

Preferred embodiments include the following:

(a) an agent or combination of agents wherein the serotonin agonist exhibits only central serotonergic actions; or (b) an agent or combination of agents wherein the serotonin agonist exhibits only central 5-hydroxytryptamine-2 actions; or (c) an agent or combination of agents wherein the prostanoid antagonist exhibits only peripheral actions while the serotonin agonist exhibits only central actions; or (d) an agent or combination of agents wherein the cannabimimetic agent is a cannabinoid CB1 receptor agonist; or (e) an agent or combination of agents wherein the cannabimimetic agent is a cannabinoid CB2 receptor agonist; or (f) an agent or combination of agents wherein the cannabimietic agent is a non-selective cannabinoid receptor agonist; or (g) an agent or combination of agents wherein the cannabimimetic agent is an endocannabinoid; or (h) an agent or combination of agents wherein the cannabimimetic agent is an inhibitor of cannabinoid breakdown; or (i) an agent or combination of agents wherein the cannabimimetic agent is an inhibitor of endocannabinoid membrane transport; or (j) an agent or combination of agents wherein the cannabimimetic agent is a cannabinoid precursor or prodrug or both; or (k) an agent or combination of agents that have the ability to induce central nervous system serotonin and/or noradrenalin release and that possess the prostanoid antagonistic profile discussed above; or (l) an agent or combination of agents that have the ability to induce central nervous system serotonin and/or noradrenalin release and possess only peripheral antagonistic effects; or (m) an agent or combination of agents that have the ability to inhibit reuptake of serotonin and/or noradrenalin and that possess the prostanoid antagonistic profile discussed above; or (n) an agent or combination of agents that have the ability to promote serotonin and/or noradrenalin release and possess only peripheral antagonistic effects.

Sleep-related breathing disorders include, but are not limited to, obstructive sleep apnea syndrome, apnea of prematurity, congenital central hypoventilation syndrome, obesity hypoventilation syndrome, central sleep apnea syndrome, Cheyne-Stokes respiration, and snoring.

As disclosed herein, conventional laboratory techniques and procedures can be generally performed according to methods well known in the art and as described in various general and more specific references that are cited and discussed throughout the present specification. Unless specific definitions are provided, the nomenclature utilized in connection with, and the laboratory procedures and techniques of, molecular biology, genetic engineering, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

In certain embodiments, the invention provides pharmaceutical compositions comprising a therapeutically effective amount, or dose, of a compound that treats sleep-related breathing disorders. As is well known in the art, such compositions can be prepared together with a pharmaceutically acceptable diluent, carrier, solubilizer, emulsifier, preservative, and/or adjuvant.

As used herein, the term "agent" denotes a chemical compound, a mixture of chemical compounds, a biological macromolecule, or an extract made from biological materials.

As used herein, the term "pharmaceutical composition" refers to a composition comprising a pharmaceutically acceptable carrier, excipient, or diluent and a chemical compound, peptide, or composition as described herein that is capable of inducing a desired therapeutic effect when properly administered to a patient, specifically for treating sleep-related disorders.

As used herein, the term "therapeutically effective amount" refers to the amount of a pharmaceutical composition of the invention or a compound identified in a screening method of the invention determined to produce a therapeutic response in a mammal, specifically for treating sleep-related disorders. Such therapeutically effective amounts are readily ascertained by one of ordinary skill in the art and using methods as described herein.

As used herein, the term "substantially pure" means an object species that is the predominant species present (i.e., on a molar basis it is more abundant than any other individual species in the composition). In certain embodiments, a substantially purified fraction is a composition wherein the object species comprises at least about 50 percent (on a molar basis or on a weight or number basis) of all macromolecular species present. In certain embodiments, a substantially pure composition will comprise more than about 80%, 85%, 90%, 95%, or 99% of all macromolar species present in the composition. In certain embodiments, the object species is purified to essential homogeneity (wherein contaminating species cannot be detected in the composition by conventional detection methods) wherein the composition consists essentially of a single macromolecular species.

As used herein, the term "patient" includes human and animal subjects.

Unless otherwise required by context, singular terms shall include pluralities and plural terms shall include the singular.

As disclosed herein, an individual diagnosed with a sleep-related breathing disorder is administered either a composition or agent according to the invention having any of the foregoing pharmacological profiles in an amount effective to prevent or suppress such disorders. The specific dose may be calculated according to such factors as body weight or body surface. Further refinement of the calculations necessary to determine the appropriate dosage for treatment of sleep-related breathing disorders is routinely made by those of ordinary skill in the art without undue experimentation. Appropriate dosages may be ascertained through use of established assays for determining dosages.

Routes of administration for the foregoing methods may be by any systemic means including oral, intraperitoneal, subcutaneous, intravenous, intramuscular, transdermal, inhaled, or by other routes of administration; osmotic mini-pumps and timed-released pellets or other depot forms of administration may also be used. The pharmaceutical compositions may be administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration. The only limitation for administration route according to the methods of this invention is that the route of administration results in the ultimate delivery of the pharmacological agent to the appropriate receptor. Acceptable formulation materials preferably are nontoxic to recipients at the dosages and concentrations employed. The pharmaceutical composition can contain formulation materials for modifying, maintaining or preserving, for example, pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immnunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. (See e.g., REMINGTON'S PHARMACEUTICAL SCIENCES, 18$^{th}$ Edition, (A. R. Gennaro, ed.), 1990, Mack Publishing Company.)

Those of skill in the art also will recognize that with respect to the compounds discussed above, such compounds may contain a center of chirality. Thus, such agents may exist as different enantiomers or as enantiomeric mixtures. Use of any one enantiomer alone or contained within an enantiomeric mixture with one or more stereoisomers is contemplated by the present invention.

Optimal pharmaceutical compositions can be determined by one skilled in the art depending upon, for example, the intended route of administration, delivery format and desired dosage. See, for example, REMINGTON'S PHARMACEUTICAL SCIENCES, Id. Such compositions may influence the physical state, stability, rate of in vivo release and rate of in vivo clearance of the antibodies of the invention.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can comprise Tris buffer of about pH 7.0-8.5, or acetate buffer of about pH 4.0-5.5, which may further include sorbitol or a suitable substitute therefor. Pharmaceutical compositions of the invention can be prepared for storage by mixing the selected composition having the desired degree of purity with optional formulation agents (REMINGTON'S PHARMACEUTICAL SCIENCES, Id.) in the form of a lyophilized cake or an aqueous solution. Further, the compositions can be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 5 to about 8.

The pharmaceutical compositions of the invention can be delivered parenterally. When parenteral administration is contemplated, the therapeutic compositions for use in this invention may be in the form of a pyrogen-free, parenterally acceptable aqueous solution comprising the desired compound identified in a screening method of the invention in a pharmaceutically acceptable vehicle. A particularly suitable vehicle for parenteral injection is sterile distilled water in which the compound identified in a screening method of the invention is formulated as a sterile, isotonic solution, appropriately preserved. Preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which may then be delivered via a depot injection. Formulation with hyaluronic acid has the effect of promoting sustained duration in the circulation. Implantable drug delivery devices may be used to introduce the desired molecule.

The compositions may be formulated for inhalation. In these embodiments, an antagonist or agonist as disclosed herein can be formulated as a dry powder for inhalation, or inhalation solutions may also be formulated with a propellant for aerosol delivery, such as by nebulization. Pulmonary administration is further described in PCT Application No. PCT/US94/001875, which describes pulmonary delivery and is incorporated by reference.

The pharmaceutical compositions of the invention can be delivered through the digestive tract, such as orally. The preparation of such pharmaceutically acceptable compositions is within the skill of the art. An antagonist or agonist as disclosed herein that are to be administered in this fashion can be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the antagonist or agonist as disclosed herein. Diluents, flavorings, low melting point waxes, vegetable oils, lubricants, suspending agents, tablet disintegrating agents, and binders may also be employed.

A pharmaceutical composition can involve an effective quantity of an antagonist or agonist as disclosed herein in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are evident to those skilled in the art, including formulations involving appropriate receptor antagonists or agonists as disclosed herein in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, PCT Application No. PCT/US93/00829, which describes the controlled release of porous polymeric microparticles for the delivery of pharmaceutical compositions. Sustained-release preparations may include semipermeable polymer matrices in the form of shaped articles, e.g. films, or microcapsules, polyesters, hydrogels, polylactides (e.g., U.S. Pat. No. 3,773,919 and European Patent No. 058,481), copolymers of L-glutamic acid and gamma ethyl-L-glutamate (Sidman et al., 1983, *Biopolymers* 22: 547-556), poly (2-hydroxyethyl-methacrylate) (Langer et al., 1981, *J. Biomed. Mater. Res.* 15: 167-277 and Langer, 1982, Chem. Tech. 12: 98-105), ethylene vinyl acetate (Langer et al., id.) or poly-D(–)-3-hydroxy-butyric acid (European Patent Publication No. 133,988). Sustained release compositions may also include liposomes, which can be prepared by any of several methods known in the art. See e.g., Eppstein et al., 1985, *Proc. Natl. Acad. Sci. USA* 82: 3688-3692; European Patent Publication No. 036,676; European Patent Publication No. 088,046, and European Patent Publication No. 143,949.

Pharmaceutical compositions to be used for in vivo administration typically are sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

Once a pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

This invention further provides kits for producing a single-dose administration unit. Kits according to the invention can each contain both a first container having a dried antagonist or agonist compound as disclosed herein and a second container having an aqueous formulation, including for example single and multi-chambered pre-filled syringes (e.g., liquid syringes, lyosyringes or needle-free syringes).

An effective amount of a pharmaceutical composition of the invention to be employed therapeutically will depend, for example, upon the therapeutic context and objectives. One skilled in the art will appreciate that the appropriate dosage levels for treatment, according to certain embodiments, will thus vary depending, in part, upon the antagonist or agonist delivered, the indication for which the pharmaceutical composition is being used, the route of administration, and the size (body weight, body surface or organ size) and/or condition (the age and general health) of the patient. A clinician may titer the dosage and modify the route of administration to obtain the optimal therapeutic effect. Typical dosages range from about 0.1 µg/kg to up to about 100 mg/kg or more, depending on the factors mentioned above. In certain embodiments, the dosage may range from 0.1 µg/kg up to about 100 mg/kg; or 1 µg/kg up to about 100 mg/kg; or 5 µg/kg up to about 100 mg/kg.

Dosing frequency will depend upon the pharmacokinetic parameters of an antagonist or agonist as disclosed herein in the formulation. For example, a clinician administers the composition until a dosage is reached that achieves the desired effect. Such a composition may therefore be administered as a single dose, or as two or more doses (which may or may not contain the same amount of the desired molecule) over time, or as a continuous infusion via an implantation device or catheter. Further refinement towards establishing an appropriate dosage is routinely made by those of ordinary skill in the art and is within the ambit of tasks routinely performed by them. Appropriate dosages may be ascertained through use of appropriate dose-response data.

Pharmaceutical compositions of the invention can be administered alone or in combination with other therapeutic agents, in particular, in combination with other sleep disorder agents. Such agents can generally include sleep-inducing compounds, barbiturates, and the like.

The following references are also incorporated by reference: Bisgard et al., 1979, *Respir. Physiol.* 37: 61-80; Zucker & Cornish, 1980, *Circ. Res.* 47: 509-515; Matsumoto, 1981, *Arch. Int. Pharmacodyn. Ther.* 254: 282-292; Jacobs & Comroe, 1971, *Circ. Res.* 29: 145-155; Black et al. 1972. *Am. J. Physiol.* 223: 1097-1102; Downs et al., 1995, *Laryngoscope* 105: 857-861; Szereda-Przestaszewska & Wypych, 1995. *Respir. Physiol.* 101: 231-237; Yoshioka et al. 1992, *J. Pharmacol. Exp. Ther.* 260: 917-924; Yoshioka et al., 1992, *J. Pharmacol. Exp. Ther.* 260: 917-924; Widdop et al., 1994, *J. Auton. Nerv. Syst.* 46: 65-73; Ponsonby et al., 1997, *J. Paediatr. Child. Health* 33: 317-323; Yoshioka et al., 1992 *J. Pharmacol. Exp. Ther.* 260: 917-924; Radulovacki et al., 1998. Sleep 21: 131-136; Carley & Radulovacki, 1999, *Am. J. Respir. Crit. Care* 160: 1824-1829; Carley et al., 2001, *Pharmacol. Biochem. Behav.* 69: 283-289; Badr et al., 1994, *Am. J. Respir. Crit. Care Med.* 150: 561-564; Coon et al., 1994, *J. Appl. Physiol.* 76: 2546-2551; Fenik et al., 2004, *Arch. Ital. Biol.* 142: 237-249; Grogaard & Sundell, 1983, *Pediatr. Res.* 17: 213-219; Haniffa et al., 2004, *Cochrane Database Syst. Rev.* 4; CD003531; Lugaresi et al., 1978, In *ADVANCES IN SLEEP RESEARCH*, (Weitzman, ed.), New York: Spectrum Publications, pp. 68-70; McQueen et al., 1998, *J. Physiol.* 507: 843-855; Mendelson et al., 1988, *Physiol. Behav.* 43: 229-234; Pack, 1988, *Chest* 94: 1200-1204; Pack et al., 1990, *Prog. Clin. Biol. Res.* 345: 177-188; Phillipson, 1978, *Am. Rev. Respir. Dis.* 118: 909-939; Phillipson, 1978, *Ann. Rev. Physiol.* 40: 133-156; Planes et al., 1999, *Sleep* 22: 507-513; Sato et al., 1990, *Am. J. Physiol.* 259: R282-R287; Strohl & Thomas, 1997, *Respir. Physiol.* 110: 269-275; Thomas et al., 1992, *J. Appl. Physiol.* 73: 1530-1536; Thomas et al., 1995, *J. Appl. Physiol.* 78: 1215-1218; and Veasey et al., 1999, *Am. J. Respir. Crit. Care Med.* 160: 1659-1667.

Further aspects of the invention and embodiments will be apparent to those skilled in the art. In order that the present invention is fully understood, the following Examples are provided by way of exemplification only and not by way of limitation. The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

Example 1 describes how experimental animals are prepared for treatment with prostanoid antagonists, either alone or in combination with other agents, and subsequent physiological recording and testing.

Example 2 describes physiological recording methods used in treated and control animals and interpretation of results that can be obtained from administration of a prostanoid antagonist.

Example 3 describes interpretation of results that can be obtained from experimental animals first treated by prostanoid agonist administration followed by prostanoid receptor antagonist administration.

Example 4 describes physiological recording methods useful for treated and control animals and interpretation of results that can be obtained from administration of a prostanoid antagonist in combination with another agent.

Example 5 describes agents or compositions that possess a specific prostanoid-related pharmacological activity that is used to effectively suppress or prevent sleep-related breathing disorders.

EXAMPLE 1

Preparation of Animals for Physiological Testing and Recording

Adult, male Sprague-Dawley rats (obtained from Sasco-King, Wilmington, Mass.; usually 8 per test group; average weight=300 g) are maintained on a 12-hour light (08:00-20:00 hour)/12-hour dark (20:00-08:00 hour) cycle for one week, housed in individual cages and given ad libitum access to food and water. Following the one week of acclimatization, animals are subjected to the following surgical procedures.

Acclimatized animals are anesthetized using a mixture of ketamine (80 mg/mg) and xylazine (5 mg/kg) at a volume of 1 ml/kg body weight for the implantation of cortical electrodes for electroencephalogram (EEG) recording and neck muscle electrodes for electromyogram (EMG) recording. The surface of the skull is exposed surgically and cleaned with a 20% solution of hydrogen peroxide followed by a solution of 95% isopropyl alcohol. Next, a dental preparation of sodium fluoride (Flura-GEL®, Saslow Dental, Mt. Prospect, Ill.) is applied to harden the skull above the parietal cortex and allowed to remain in place for 5 minutes. The fluoride mixture is then removed from the skull above the parietal cortex. The EEG electrodes consisting of four stainless steel machine screws, having leads attached thereto, are threaded into the skull to rest on the dura over the parietal cortex. A thin layer of Justi® resin cement (Saslow Dental, Mt. Prospect, Ill.) is applied to cover the screw heads (of screws implanted in the skull) and surrounding skull to further promote the adhesion of the implant. EMG electrodes consisting of two ball-shaped wires are inserted into the bilateral neck musculature. All leads (i.e., EEG and EMG leads) are soldered to a miniature connector (39F1401, Newark Electronics, Schaumburg, Ill.). Lastly, the entire assembly is fixed to the skull with dental cement.

After surgery, all animals are allowed to recover for one week before being recorded for sleep and breathing.

EXAMPLE 2

Physiological Recording and Suppression of Apneas

Physiological parameters (see below) from each animal prepared as set forth in Example 1 are recorded on 2 occasions in random order, with recordings for an individual animal separated by at least 3 days. Fifteen minutes prior to each recording an animal receives a systemic injection (1 ml/kg intraperitoneal bolus) of either saline (control) or an active dose of a drug treatment.

Respiration is recorded by placing each animal, unrestrained, inside a single chamber plethysmograph (PLYUN1R/U; Buxco Electronics, Sharon, Conn.; dimension 6 in. ×10 in.×6 in.) ventilated with a bias flow of fresh room air at a rate of 2 L/min. A cable plugged onto the animal's connector and passed through a sealed port is used to collect the bioelectrical activity from the head implant. Respiration, EEG activity, and EMG activity are displayed on a video monitor and simultaneously digitized 100 times per second and stored on computer disk (Experimenter's Workbench; Datawave Technologies, Longmont, Colo.).

Sleep and waking states are assessed using software developed by Benington et al. (1994, *Sleep* 17: 28-36) to analyze the biparietal EEG and nuchal EMG signals on 10-second epochs. This software discriminates wakefulness (W) as a high frequency low amplitude EEG with a concomitant high EMG tone, NREM sleep by increased spindle and theta activity together with decreased EMG tone, and REM sleep by a low ratio of a delta to theta activity and an absence of EMG tone. Sleep efficiency is measured as the percentage of total recorded epochs staged as NREM or REM sleep.

An accepted physiological animal model of spontaneous sleep apnea in the rat (see Radulovacki & Carley, 2002, in SLEEP-RELATED BREATHING DISORDERS: EXPERIMENTAL MODELS AND THERAPEUTIC POTENTIAL, (Carley & Radulovacki, eds.), Marcel Dekker: New York, pp. 3-16) is used to assess the effects of test drugs. More specifically, sleep apneas, defined as cessation of respiratory effort for at least 2.5 seconds, are scored for each recording session and associated with the stage of sleep in which they occur (i.e., NREM or REM sleep). The duration requirement of 2.5 seconds represents at least 2 "missed" breaths, which is therefore analogous to a 10 second apnea duration requirement in humans, which also reflects 2-3 missed breaths. The events detected represent central apneas because decreased ventilation associated with obstructed or occluded airways would generate an increased plethysmographic signal, rather than a pause. Apnea indexes (AI), defined as apneas per hour in a stage are separately determined for NREM and REM sleep. The effects of sleep stage (NREM vs. REM) and injection (control vs. dose of active test drug) are tested using ANOVA with repeated measures. Multiple comparisons are controlled using Fisher's protected least significant difference (PLSD) test. In addition, the timing and volume of each breath are scored by automatic analysis (Experimenter's Workbench; Datawave Technologies, Longmont, Colo.). For each animal the mean respiratory rate (RR) and minute ventilation (MV) are computed for W (wakefulness) throughout the 6 hour control recording and used as a baseline to normalize respiration during sleep and during active drug administration in that animal. One-way ANOVA is also performed by non-parametric (Friedman) analysis. Conclusions using parametric and non-parametric ANOVA are compared in all cases.

Results of the administration of prostanoid receptor antagonists on the rate of apneas per hour of NREM and REM sleep during the 6 hours of polygraphic recording that demonstrate a significant suppression ($p<0.05$) are indicative of efficacy against sleep apnea and other sleep-related breathing disorders. According to this approach, ramatroban, Ifetroban, diphloretin phosphate, polyphloretin phosphate and seratrodast, all demonstrate dose-dependent efficacy against sleep apnea.

Those of skill in the art will recognize that exemplary prostanoid receptor antagonists, including, but not limited to, any of the prostanoid receptor antagonists mentioned above, and the like may be used to prevent or ameliorate sleep-related breathing disorders. Further, those of skill in the art will also recognize that the results that are obtained using this animal model can be readily correlated to other mammals, especially primates (e.g., humans).

EXAMPLE 3

Induction and Suppression of Sleep Apneas

Administration of prostanoid antagonists or prostanoid agonists alone and in combination to produce respiratory responses in anesthetized animals is performed as set forth above in Example 2. An increased rate of sleep apneas after a prostanoid agonist and a blockade of this effect by treatment with a prostanoid antagonist is indicative of the therapeutic efficacy of the antagonist to treat sleep apnea and other sleep-related breathing disorders.

Overall, exacerbation of spontaneous apnea during sleep produced by peripherally administered prostanoid agonists and a blockade of this effect by prostanoid antagonists indicate a physiological role for prostanoid in regulating breathing and therapeutic efficacy of treating sleep apnea by prostanoid antagonists.

EXAMPLE 4

Suppression of Sleep Apneas by a Prostanoid Antagonist in Combination with a Second Agent Administration of prostanoid antagonists alone and in combination with other agents (e.g., including, but not limited to, serotonin agonists, cannabimimetics, SSRIs, or SNRIs) to produce respiratory responses in anesthetized animals is performed as set forth above in Example 2. Isobolographic analysis is used as an accepted, art-recognized and definitive standard for detecting and characterizing drug interactions (Luszczki & Czuczwar, 2003, *Epilepsy Res.* 56: 27-42). Recently, an "interaction index" has been proposed (Tallarida, 2002, *Pain* 98: 163-168) to quantify drug synergism, and this index is also useful to characterize synergism when one of the two compounds lacks independent efficacy (e.g., an SSRI; see Kraiczi et al., 1999, *Sleep* 22: 61-66). Isobolographic analysis and the interaction index rely on statistical estimation of the $ED_{50}$. Thus, it is important to have adequate power in the preclinical tests to confidently measure a 50% reduction in apnea expression. For this form of efficacy determination, dose-dependent changes in sleep apnea expression are determined for each agent (i.e., the prostanoid antagonist and the second agent) alone and combined in various ratios.

A decreased rate of sleep apneas after administration of any formulation (comprising one or a combination of prostanoid antagonists alone or in combination with serotonin agonists, cannabimimetics, SSRIs, or SNRIs as disclosed above) is indicative of the therapeutic efficacy of the formulation to treat sleep apnea and other sleep-related breathing disorders. In particular, a preferred combination of agents exhibits greater suppression of apneas than either agent alone, or equivalent suppression of apneas at lower doses than either agent alone.

EXAMPLE 5

Suppression or Prevention of Sleep Apneas

As indicated by the examples above, prostanoids can play an important role in apnea genesis. More specifically, the nodose ganglia of the vagus nerves appear to be a crucial target site for prostanoid receptor antagonists.

Therefore, in view of the foregoing, sleep related breathing disorders (sleep apnea syndrome, apnea of infancy, Cheyne-Stokes respiration, sleep-related hypoventilation syndromes) can be effectively prevented or suppressed via systemic administration of pharmacological agents exhibiting antagonism at one or more prostanoid receptors.

Effective treatment for the prevention or suppression of sleep related breathing disorders can include, but are not limited to, systemic and local administration of a prostanoid receptor antagonist or a combination of antagonists. Such prostanoid receptor antagonists can be administered in combination with one or more of the other compounds disclosed herein, including, but not limited to, serotonin re-uptake inhibitors (SSRI) or serotonin/noradrenalin reuptake inhibitors (SNRI), serotonin receptor agonists, compounds with cannabinoid receptor subtype 1 or cannabinoid receptor subtype 2 activity, endocannabinoid breakdown inhibitors, cannabimimetic agents, compounds that inhibit the synthesis of prostanoids, and the like. Preferably, the compounds will have activity in the peripheral nervous system and will not cross the blood-brain barrier.

Pharmacological treatments other than prostanoid receptor antagonism may also be used to enhance prostanoid receptor antagonism (See e.g. U.S. Pat. No. 6,331,536). Specifically, antagonism of presynaptic $\alpha_2$ adrenergic receptors located on brain stem serotonergic neurons (heteroreceptors) enhances serotonin release. Selective receptor antagonists have been shown to block presynaptic and postsynaptic receptors (See e.g., de Boer, 1996, *J. Clin. Psychiatry* 57: 19-25; Devane, 1998, *J. Clin. Psychiatry* 59: 85-93; Puzantian, 1998, *Am. J. Health Syst. Pharm* 55: 44-49; and the like). Central serotonin release is increased with minimal adrenergic side effects, such as hypertension, because the affinity of such agents for central $\alpha_2$ receptors in about 10 times higher than for peripheral $\alpha_2$ receptors. Therefore, because these agents are high affinity antagonists at 5-hydroxytryptamine $_{2A}$, 5-hydroxytryptamine $_{2C}$, and 5-hydroxytryptamine $_3$ receptors, the net effect is increased post-synaptic 5-hydroxytryptamine $_1$ activity within the brain and reduced 5-hydroxytryptamine $_2$ and 5-hydroxytryptamine $_3$ post-synaptic activity in the central and peripheral nervous systems. Each of these pharmacological effects serves to stimulate respiration and suppress apnea.

An individual diagnosed with a sleep related breathing disorder can be administered a compound, composition, agent or formulation thereof having any of the pharmacological activities disclosed herein, namely prostanoid receptor antagonists, etc., in an amount effective to prevent or suppress such sleep related breathing disorders. The specific dose can be calculated as disclosed herein according to body weight or body surface. Appropriate dosages can be determined through the use of established assays for setting dosages. The pharmacological treatment can be administered to the person, patient, or subject in need of such treatment immediately before sleep or at any time prior to sleep with the appropriate slow release or delayed release dosage forms as required for the circumstances. The effect of such pharmacological treatment will be the alleviation, amelioration, suspension, and/or cessation of the sleep related breathing disorder(s) of the person, patient, or subject.

Figure 1:
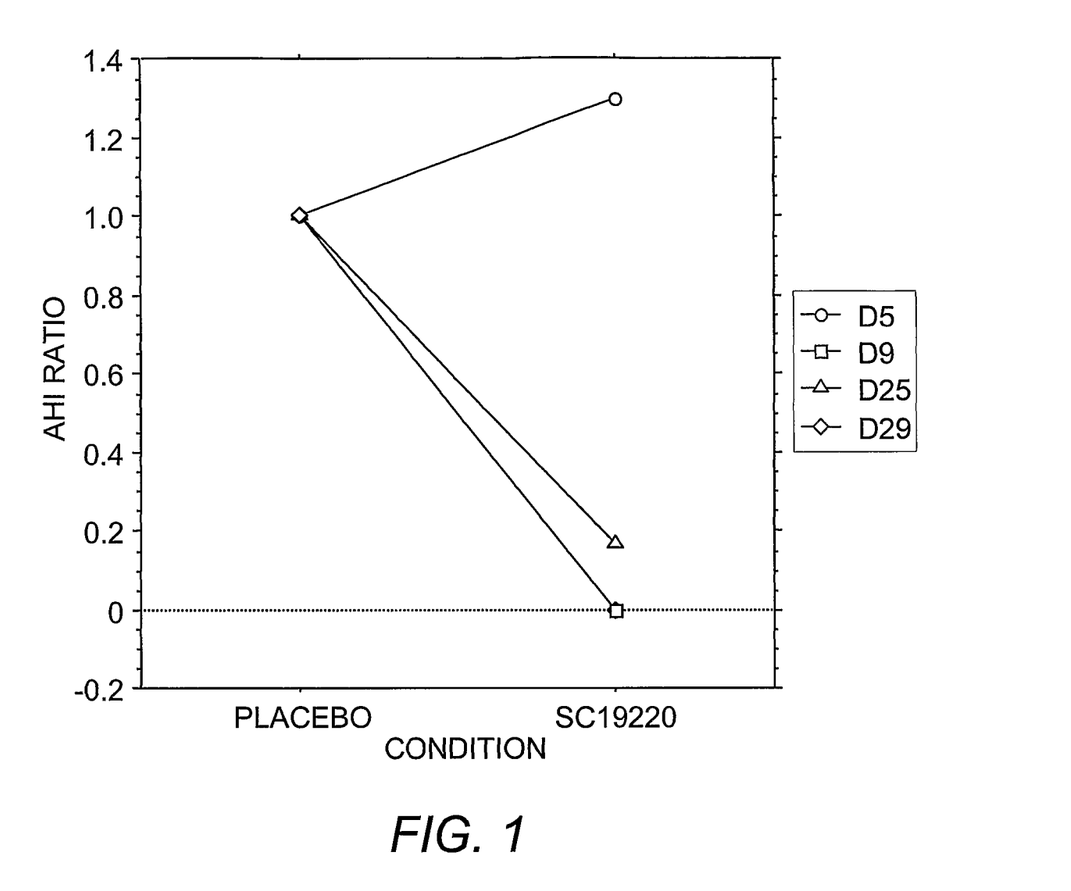
FIG. 1 shows suppression of apnea by a prostanoid receptor antagonist. The graph shows the apnea-hypopnea index (AHI) ratio of four test subjects (D5, D9, D25, and D29) receiving SC19220 as compared to placebo.

By way of illustration, suppression of apnea was demonstrated using $EP_1$ prostanoid receptor antagonist, SC19220 (DelToro, F., 2000, *Cell Physiol.* 182:196). SC19220 administered by intraperitoneal injection at a dose of 0.005 mg/kg reduced apnea frequency with respect to placebo (DMSO) control injection in each of 4 test animals (FIG. 1). The average reduction was 64% and in 2 of 4 animals apnea was eliminated throughout the 6-hour recording. These observations demonstrate the utility of employing prostanoid receptor antagonists to ameliorate or eliminate the expression of sleep-related apnea.

All patents, patent applications, and other scientific and/or technical writings mentioned herein are incorporated by reference to the extent that they are not contradictory.

The foregoing description of preferred embodiments of the invention is presented for purposes of illustration and description, and is not intended to be exhaustive or to limit the invention to the precise form or forms disclosed. The description is selected to best explain the principles of the invention and practical application of these principles to enable others skilled in the art to best utilize the invention in various embodiments and various modifications as are suited to a particular use contemplated. The scope of the invention is not to be limited by the specification, but defined by the claims set forth below.

We claim:

1. A method for ameliorating a sleep-related breathing disorder, the method comprising the step of administering an effective dose of one or more prostanoid receptor antagonists to a patient in need thereof, wherein said prostanoid receptor antagonist is selected from the group consisting of ramatroban, ifetroban, seratrodast, diphloretin phosphate, polyphloretin phosphate, or SC19220.

* * * * *